United States Patent
Yamada et al.

(10) Patent No.: US 11,147,453 B2
(45) Date of Patent: Oct. 19, 2021

(54) CALIBRATION FOR OCT-NIRAF MULTIMODALITY PROBE

(71) Applicant: Canon U.S.A., Inc., Melville, NY (US)

(72) Inventors: Daisuke Yamada, Cambridge, MA (US); Jeffrey Chen, Winchester, MA (US); Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 725 days.

(21) Appl. No.: 15/724,003

(22) Filed: Oct. 3, 2017

(65) Prior Publication Data

US 2019/0099079 A1     Apr. 4, 2019

(51) Int. Cl.
*A61B 5/00*     (2006.01)
*G01B 9/02*     (2006.01)
*G01N 21/64*    (2006.01)

(52) U.S. Cl.
CPC .......... *A61B 5/0035* (2013.01); *A61B 5/0066* (2013.01); *A61B 5/0071* (2013.01);
(Continued)

(58) Field of Classification Search
CPC .... A61B 2560/0223; A61B 2562/0233; A61B 2562/228; A61B 2576/00; A61B 5/0035;
(Continued)

(56) References Cited

U.S. PATENT DOCUMENTS 5,303,026 A    4/1994   Strobi et al.
6,763,261 B2   7/2004   Casscells, III et al.
(Continued)

FOREIGN PATENT DOCUMENTS

EP    2846149 A1    3/2015
JP    2006061683 A  3/2006
(Continued)

OTHER PUBLICATIONS

Wang, H., "Near infrared autofluorescence augmentation of optical coherence tomography for diagnosis of coronary atherosclerosis", Thesis/Dissertation, Boston University College of Engineering, 2014.
(Continued)

*Primary Examiner* — Joanne M Hoffman
*Assistant Examiner* — Alexei Bykhovski
(74) *Attorney, Agent, or Firm* — Canon U.S.A., Inc., IP Division

(57) ABSTRACT

A multimodality system includes first and second modalities, a catheter, and a processor. The catheter collects fluorescent light from a plurality of locations of a sample which has been irradiated with excitation light of the second modality; a detector detects intensity of the fluorescent light received from the plurality of locations as a function of an angle α formed between the normal to the sample surface and the optical axis of the excitation light. A processor calculates the angle α at each of the plurality of locations based on radiation of the first modality incident on the sample, and corrects the intensity of the detected fluorescent light using a calibration factor $g(\alpha)$. The calibration factor $g(\alpha)$ is a function of the angle α calculated at two or more of the plurality of locations. The angle α is composed of a transversal angle $\alpha_t$ and an axial angle $\alpha_a$.

13 Claims, 11 Drawing Sheets

(52) U.S. Cl.
CPC .......... *A61B 5/0086* (2013.01); *A61B 5/6852* (2013.01); *G01B 9/0203* (2013.01); *G01B 9/02091* (2013.01); *G01N 21/6458* (2013.01); *A61B 2560/0223* (2013.01); *A61B 2562/0233* (2013.01); *A61B 2562/228* (2013.01); *A61B 2576/00* (2013.01); *G01B 9/02067* (2013.01); *G01N 21/6486* (2013.01); *G01N 2021/6465* (2013.01); *G01N 2021/6484* (2013.01); *G01N 2201/127* (2013.01)

(58) Field of Classification Search
CPC ... A61B 5/0066; A61B 5/0071; A61B 5/0086; A61B 5/6852; G01B 9/0203; G01B 9/02067; G01B 9/02091; G01N 2021/6465; G01N 2021/6484; G01N 21/6458; G01N 21/6486; G01N 2201/127
See application file for complete search history.

(56) References Cited

U.S. PATENT DOCUMENTS

| | | |
|---|---|---|
| 7,428,048 B1 | 9/2008 | Farkas et al. |
| 7,447,408 B2 | 11/2008 | Bouma et al. |
| 7,508,524 B2 | 3/2009 | Mahadevan-Jansen et al. |
| 7,749,168 B2 | 7/2010 | Maschke et al. |
| 7,872,759 B2 | 1/2011 | Tearney et al. |
| 7,889,348 B2 | 2/2011 | Tearney et al. |
| 7,952,706 B2 | 5/2011 | Ling et al. |
| 7,952,719 B2 | 5/2011 | Brennan, III |
| 8,035,819 B2 | 10/2011 | Zuluaga |
| 8,084,755 B2 | 12/2011 | Hall et al. |
| 8,190,241 B2 | 5/2012 | Ntziachristos et al. |
| 8,208,995 B2 | 6/2012 | Tearney et al. |
| 8,219,183 B2 | 7/2012 | Maschke et al. |
| 8,289,522 B2 | 10/2012 | Tearney et al. |
| 8,553,219 B2 | 10/2013 | Patil et al. |
| 8,928,889 B2 | 1/2015 | Tearney et al. |
| 9,179,845 B2 | 11/2015 | Farcy et al. |
| 9,254,102 B2 | 2/2016 | Tearney et al. |
| 9,286,673 B2 | 3/2016 | Begin et al. |
| 9,295,391 B1 | 3/2016 | Tearney et al. |
| 9,332,942 B2 | 5/2016 | Jaffer et al. |
| 9,526,424 B2 | 12/2016 | Judell et al. |
| 9,557,154 B2 | 1/2017 | Tearney et al. |
| 9,713,488 B2 | 7/2017 | Hutchinson |
| 9,763,623 B2 | 9/2017 | Tearney et al. |
| 9,795,301 B2 | 10/2017 | Fleming et al. |
| 9,869,828 B2 | 1/2018 | Altshuler |
| 10,130,259 B2 | 11/2018 | Lam et al. |
| 10,912,462 B2 | 2/2021 | Wang et al. |
| 2008/0228086 A1 | 9/2008 | Ilegbusi et al. |
| 2009/0192358 A1 | 7/2009 | Jaffer et al. |
| 2010/0315632 A1 | 12/2010 | Brennan, III |
| 2011/0292400 A1 | 12/2011 | Fleming et al. |
| 2012/0101374 A1 | 4/2012 | Tearney et al. |
| 2014/0180133 A1 | 6/2014 | Brennan et al. |
| 2014/0276011 A1 | 9/2014 | Schmitt et al. |
| 2015/0080686 A1 | 3/2015 | Karlheinz et al. |
| 2016/0038029 A1 | 2/2016 | Darne et al. |
| 2016/0228097 A1 | 8/2016 | Jaffer et al. |
| 2017/0135584 A1 | 5/2017 | Tearney et al. |
| 2017/0209049 A1 | 7/2017 | Wang et al. |
| 2018/0055953 A1 | 3/2018 | Jaffer et al. |
| 2018/0136129 A1 | 5/2018 | Rizo et al. |
| 2018/0348439 A1 | 12/2018 | Yamada |
| 2019/0059734 A1 | 2/2019 | Yamada |
| 2019/0391338 A1 | 12/2019 | Tearney et al. |

FOREIGN PATENT DOCUMENTS

| | | | | |
|---|---|---|---|---|
| JP | 2006194812 A | | 7/2006 | |
| JP | 2008229025 A | * | 3/2007 | ............... A61B 1/00 |
| JP | 2008-229025 A | | 10/2008 | |
| JP | 2014124480 A | | 7/2014 | |
| JP | 2017-023604 A | | 2/2017 | |
| WO | 2012/039679 A2 | | 3/2012 | |
| WO | 2016/015052 A1 | | 1/2016 | |
| WO | 2016/036314 A1 | | 3/2016 | |

OTHER PUBLICATIONS

Dixon, A.J., et al. "Intravascular near-infrared fluorescence catheter with ultrasound guidance and blood attenuation correction", J. Biomed Opt., May 2013, vol. 18, No. 5.

Ughi, G.J., et al, "Dual modality intravascular optical coherence tomography (OCT) and near-infrared fluorescence (NIRF) imaging: a fully automated algorithm for the distance-calibration of NIRF signal intensity for quantitative molecular imaging", Int J Cardiovasc Imaging, Feb. 2015, pp. 259-268, vol. 31, No. 2.

Wang, H., et al, "Ex vivo catheter-based imaging of coronary atherosclerosis using multimodality OCT and NIRAF excited a 633 nm", Biomedical Optical Express, Apr. 1, 2015, pp. 1363-1375, vol. 6, No. 4.

Liu, S. et al, "Analysis and compensation for the effect of the catheter position on image intensities in intravascular optical coherence tomography", Journal of Biomedical Optics, Dec. 2016, vol. 21, No. 12.

Yoo, H., et al, "Intra-arterial catheter for simultaneous microstructural and molecular imaging in vivo", Nat Med, 2012, pp. 1680-1684, vol. 17, No. 12.

Ma, D., et al., "Rotational Multispectral Fluorescence Lifetime Imaging and Intravascular Ultrasound: Bimodal System for Intravascular applications", Journal of Biomedical Optics, Jun. 2014, pp vol. 19, No. 6.

Scolaro, L., et al., "Molecular Imaging Needles: Dual-Modality Optical Coherence Tomography and Fluorescence maging of Labeled Antibodies deep in tissue", Biomedical Optics Express, May 1, 2015, pp. 1767-1781, vol. 6, No. 5.

* cited by examiner $$\alpha_t = |\phi - \theta_{offset}|$$

$$\theta_{offset} = \tan^{-1}(h/\delta)$$
$$h = (d - d_{prev\_a})\cos(\theta_{offset})$$
$$\alpha_t = |\phi - \tan^{-1}(h/D)|$$
$$\alpha_t = |\tan^{-1}((d - d_{prev\_a})\cos(\theta_{offset})/D) - \theta_{offset}|$$

$$\alpha_a = |\pi/2 - \beta|$$
$$\beta = \sin^{-1}(d*\sin(\theta)/A)$$
$$A^2 = d_{prev}^2 + d^2 - 2d_{prev}d\cos(\theta)$$

$$\alpha = \tan^{-1}[\text{sqrt}(\tan^2(\alpha_a) + \tan^2(\alpha_t))]$$

CALIBRATION FOR OCT-NIRAF MULTIMODALITY PROBE

BACKGROUND

Field

The disclosure of this patent application relates generally to optical imaging, and in particular it relates to a multimodality imaging system for imaging bodily lumens of a subject and methods thereof for calibrating the system.

Related Art

Fiber-based optical coherence tomography (OCT) probes, such as catheters and endoscopes, have been developed to access and image internal organs of humans and animals, and are now commonly used in various medical fields. OCT is a medical imaging technique for non-invasive imaging based on low-coherence interferometry employing near-infrared light. The OCT device produces three-dimensional (3D) images, with a resolution typically of a few microns. Spectral-domain OCT (SD-OCT) is a form of OCT in which the interferometric signal between a reference beam and the back-scattered component of a sample (probe) beam reflected from a sample is split into its frequency components by a dispersive device and collected by an optical detector (line camera). The collected data contains the spectral information of the backscattered signal. This spectral data can be transformed to the spatial domain to obtain a one-dimensional (1D) spatial distribution, referred to as an A-scan, representative of the scattering properties of the sample. Scanning the sample beam across the sample produces a series of adjacent A-scans which can then be used to create a two-dimensional (2D) tomogram, called a B-scan. A volume representation can be acquired by further scanning the sample beam in a third direction (depth) of the sample to collect a series of B-scans that covers the three-dimensional (3D) volume of interest.

An OCT catheter, which generally comprises a sheath, a coil and an optical probe, is navigated through a lumen, by manual or automatic control. In order to acquire cross-sectional images of tubes and cavities such as vessels, esophagus and nasal cavity, generally referred to as "bodily lumens", the optical probe is rotated with a fiber optic rotary joint (FORJ). In addition, the optical probe is simultaneously moved (translated) longitudinally during the rotation so that images are obtained in a helical scanning pattern. This longitudinal movement is most commonly performed by mechanically pulling the tip (distal end) of the probe back towards the proximal end and therefore this process is referred to as a "pullback" operation. The rotation and translation movements of the OCT catheter scans the optical probe helically inside the bodily lumen, and produces a series of adjacent helical A-scans of the sample which can then be used to create a helical two-dimensional (2D) tomogram. Moving the catheter in a third direction within the bodily lumen (changing the distance of the catheter with respect to the wall of the lumen) allows the collection of a series of B-scans which can be combined to form a three-dimensional (3D) image of the sample of interest.

Conventionally, while techniques such as OCT as well as other imaging techniques including intervascular ultrasound (IVUS) have been well established as being capable of visualizing morphologic features and depth of bodily lumens, these techniques have not been shown to identify chemicals/molecules associated with the health status of such morphologic features. In particular, the high scattering nature of bodily lumens and liquids contained therein (e.g., blood) prevent OCT from identifying important health-related parameters of imaged samples. However, determining the functional properties as well as chemical and molecular composition of tissues is as important as the structure revealed by the backscattered intensity. In recent years, to compliment this perceived deficiency of OCT, it has been proposed to add a secondary modality to OCT. Using a second imaging modality such as near-infrared autofluorescence (NIRAF) or near-infrared fluorescence (NIRF) spectroscopy with OCT has the potential to improve imaging and diagnosis results.

Intravascular fluorescence is a catheter-based molecular imaging technique that uses near-infrared fluorescence to detect artery wall autofluorescence (NIRAF) or induced fluorescence (NIRF) generated by molecular agents injected intravenously. Intravascular fluorescence typically uses near-infrared laser-light to stimulate fluorescence emission (autofluorescence) of particular plaque components formed on a vessel wall, or to generate fluorescence from molecular- or cellular-specific agents previously injected into a vessel or artery. Fluorescence detection can be obtained by integration over a short period of time of the emitted intensity based on the fluorescence life-time (of the particular plaque component or molecular agent), or by analyzing the spectral shape of emitted fluorescence (fluorescence spectroscopy). Imaging catheters contain an optical fiber and related optics to deliver and collect light to and from the inner lumen of a body. Therefore, a multimodality device including OCT or IVUS and NIRAF/NIRF imaging elements have been recently proposed. See list of non-patent literature (NPL) documents listed herein below.

NIRAF detection used as a second imaging modality with OCT has the potential to improve diagnosis of necrotic core lesions and other parameters. To improve image accuracy and diagnosis, the detected OCT and NIRAF signals need to be properly synchronized and calibrated. State of the art calibration for NIRAF signal involves calibrating for the detected signal as a function of distance between the catheter and blood vessel wall. However, calibrating the detected NIRAF/NIRF signal using distance alone, as described in NPL1 by Wang et al., does not consider other factors that affect the signal. The detected NIRAF/NIRF signal is also a function of the angle between the optical axis of the excitation light and the normal line to the sample surface, among other factors. Without correction for the angle, the NIRAF data will be less accurate and the desired improvement in imaging and diagnosis may not be achieved.

SUMMARY

The present patent application aims to improve on the above-described state of the art. According to an aspect of the present application, a multimodality system detects NIRAF or NIRF light intensity from a sample that has been irradiated with excitation light; using the angle between the optical axis of the excitation light and the normal line to the sample surface the NIRAF signal is calibrated; calibration may also be achieved using depth of signal and composition of tissue. In alternative embodiments, IVUS can be used instead of OCT to calibrate for distance, angle, depth, and composition of tissue.

According to one aspect of the present invention, an apparatus comprises a catheter, a detector, and a processor. The catheter has a proximal end and a distal end arranged along an axis, and includes one or more optical channels configured to transmit therethrough radiation of at least three different wavelengths. The catheter is configured to direct radiation of first wavelength and radiation of second wavelength from its distal end thereof towards a sample along a line transverse to the axis, and is configured to collect at its distal end thereof radiation of third wavelength from a plurality of locations of the sample emitted in response to the sample being irradiated with the second wavelength. The detector is configured to detect intensity of the collected radiation of third wavelength as a function of an angle $\alpha$ formed at each of the plurality of locations between the normal to the sample surface and the optical axis of the radiation incident on the sample. The processor is configured to calculate the angle $\alpha$ at each of the plurality of locations based on the radiation of first wavelength incident on the sample, and adjust the intensity of the radiation of third wavelength detected by the detector using a calibration factor $g(\alpha)$. The calibration factor $g(\alpha)$ is function of the angle $\alpha$ calculated at each of the plurality of locations, and the processor adjusts the intensity of the radiation of third wavelength by multiplying the detected intensity by the calibration factor obtained at each of the plurality of locations.

According to another aspect of the present invention, a multimodality system includes first and second modalities, a catheter, and a processor. The catheter is configured to direct radiation from the first and second modalities onto a plurality of locations of a sample, and to collect fluorescent light emitted in response to irradiating the sample with the radiation of the second modality. A detector is configured to detect intensity of the fluorescent light received from the plurality of locations as a function of an angle $\alpha$ formed at each of the plurality of locations between the normal to the sample surface and the optical axis of the radiation incident on the sample. The processor is configured to calculate the angle $\alpha$ at each of the plurality of locations based on the radiation incident on the sample, and to adjust the intensity of the fluorescent light detected by the detector using a calibration factor $g(\alpha)$. The calibration factor $g(\alpha)$ is function of the angle $\alpha$ calculated at two or more of the plurality of locations.

Notably, the angle $\alpha$ is composed of a transversal angle $\alpha_t$ and an axial angle $\alpha_a$. The processor calculates the transversal angle $\alpha_t$ using sequential readings of the radiation of first wavelength or radiation of second wavelength backscattered from the plurality of locations detected along a pullback path of the catheter for a fixed axial rotation angle, and calculates the axial angle $\alpha_a$ using sequential readings of the radiation of first wavelength or radiation of second wavelength backscattered from the plurality of locations detected as the catheter is simultaneously rotated and pulled back.

Further features and advantageous of the invention will become apparent to those skilled in the art from the following description of exemplary embodiments with reference to the attached drawings.

DETAILED DESCRIPTION

Figure 1:
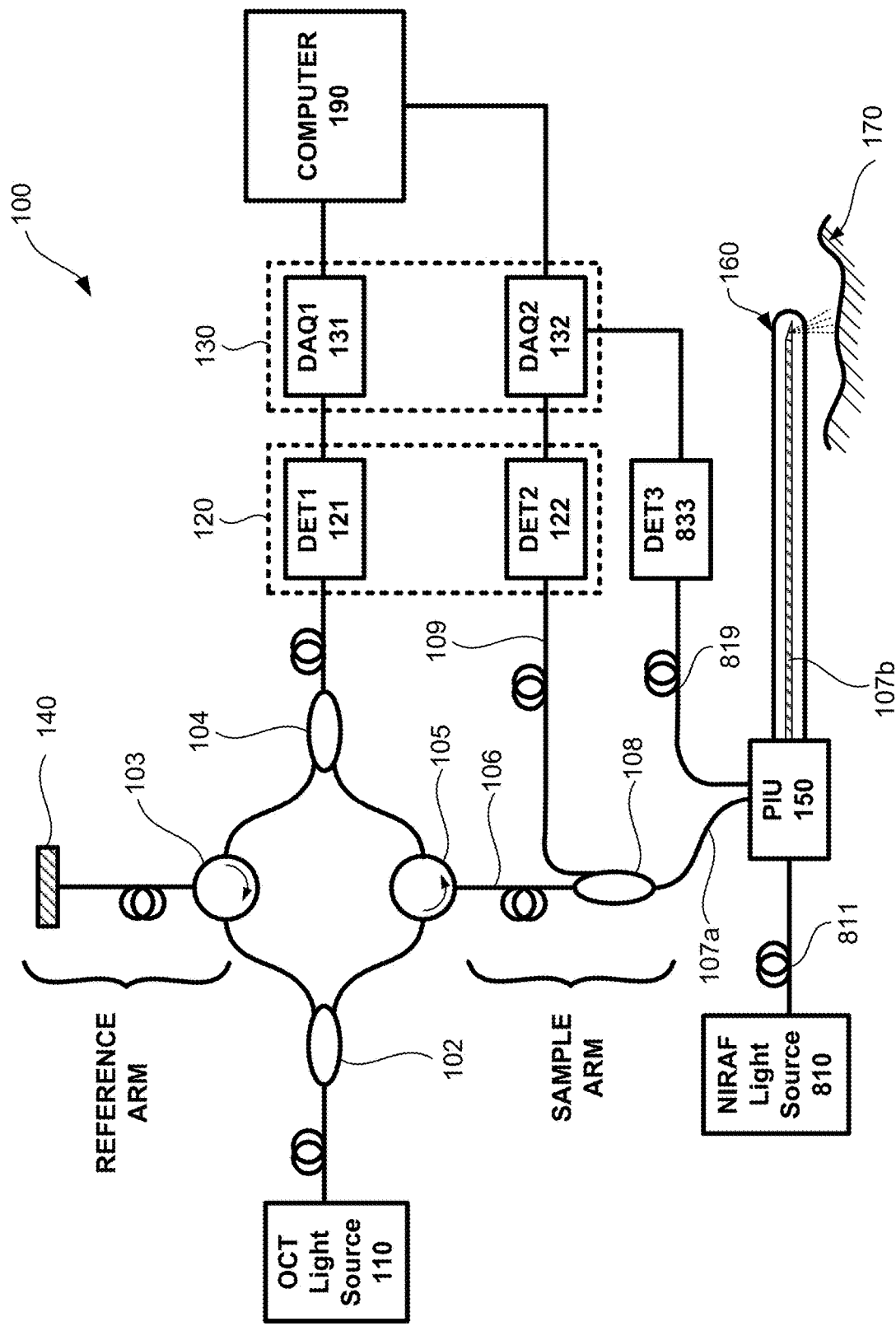
FIG. 1 illustrates an exemplary multimodality OCT-NIRAF system for imaging coronary arteries or other bodily lumens.

In the following description, reference is made to the accompanying drawings which are illustrations of embodiments in which the disclosed invention may be implemented and practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail as not to unnecessarily lengthen the present disclosure. Some embodiments of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage devices such as a magnetic or optical disk and disk drive for storing information and instructions, an optional user output device such as a display device (e.g., a monitor) for displaying information to a user, an optional user input device including alphanumeric and function keys (e.g., a keyboard) for communicating information and command selections to the processor, and an optional user input device such as a pointing device (e.g., a mouse) for communicating user input information and command selections to the processor.

As will be appreciated by those skilled in the art, the present examples may be embodied as a system, method or computer program product. Accordingly, some examples may take the form of an entirely hardware embodiment, an entirely software embodiment (including firmware, resident software, micro-code, etc.) or an embodiment combining software and hardware aspects that may all generally be referred herein as a "circuit", "module" or "system". Further, some embodiments may take the form of a computer program product embodied in any non-transitory tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that when executed by a computer or other programmable data processing apparatus causes the computer or processing apparatus to function in a particular manner, such that the instructions stored in the computer-readable media constitute an article of manufacture including instructions and processes which implement the function/act/step specified in the flowchart and/or block diagram.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without departing from structural or functional meaning.

Exemplary embodiments are described below in more detail with reference to the several drawings where like reference numerals refer to like parts.

<OCT-NIRAF System>

FIG. 1 illustrates an exemplary system 100 including an interferometric OCT modality and a NIRAF/NIRF spectroscopic modality that can be applied as an intravascular OCT-NIRAF system for imaging of coronary arteries or other bodily lumens. For example, the system 100 may also be adapted to be used for esophageal imaging. As depicted in FIG. 1, the system 100 includes an OCT modality comprised of interferometer having a sample arm and a reference arm, a light source 110, a detector unit 120, data acquisition electronics 130, and a computer 190. The sample arm includes a patient interface unit (PIU) 150 and a catheter 160. In addition, the system 100 includes a NIRAF/NIRF modality comprised of a light source 810 also connected to the catheter 160 via a fiber 811, and to computer 190 via the PIU 150. In one embodiment, the system 100 uses a swept-source laser (1310 nm+/−50 nm) as the OCT light source, and a 633 nm HeNe laser as the NIRAF/NIRF light source. The distal optics of the catheter 160 includes a double clad fiber (DCF) with a polished ball lens at the tip thereof for side-view imaging. The distal optics may alternatively include a DCF, a GRIN lens, and a refractive element (grating). OCT and NIRAF data are obtained simultaneously.

Light (radiation of first wavelength) from the light source 110 is guided through the sample arm to a sample 170, and through the reference arm to a reflector 140, to thereby generate OCT interference patterns. Specifically, light from the light source 110 is split by a splitter 102 (fiber splitter or beam splitter) into a sample beam and a reference beam which are respectively conveyed to the sample arm and the reference arm via respective optical fibers. In the sample arm, the sample beam enters a circulator 105, passes to a fiber coupler 108 via a single-mode (SM) fiber 106, and the sample beam is delivered to the catheter 160 via a double clad fiber 107a. The catheter 160 is connected to the PIU 160, and the PIU 160 is in turn connected to computer 190. Under control of the computer 190, the PIU 160 controls the sample beam to irradiate the sample 170 in a scanning manner. Light of the sample beam reflected and/or scattered by the sample 170 is collected by optics (an optical probe) arranged at the distal end of the catheter 160, and the collected light is transmitted back through a double clad fiber 107b to the PIU 150 and to fiber coupler 108. The fiber coupler 108 couples one part of the sample beam towards the circulator 105 via the SM fiber 106; and the circulator 105 guides the one part of the sample beam to the combiner 104. In addition, the fiber coupler 108 couples another part of the sample beam to a second detector 122 (second detector) via a multi-mode fiber 109.

In the reference arm, light of the reference beam enters a circulator 103 and is delivered to the reflector 140 via a non-labeled optical fiber. In the case of Time Domain OCT imaging, the reflector 140 may be implemented as a scanning mirror. And, in the case of Frequency Domain OCT (FD-OCT) imaging, the reflector 140 may be implemented as a stationary mirror. Light of the reference beam reflected from the reflector 140 passes through the circulator 105, and is also guided to the combiner 104. In this manner, the sample and reference beams are combined at the beam combiner 104 and then detected by detector 121 to generate interference signals according to known OCT principles.

A fiber optic circulator (e.g., circulator 103 or 105 in FIG. 1) is a passive, polarization-independent, three-port device that acts as a signal router. Light from a first fiber is input to the circulator via a first port and directed to a second fiber via a second port. Light returning through the second fiber is redirected to a third fiber via a third port with virtually no loss. That is, light input into the first port is not directly coupled into the third port fiber, and light input into the second port is not coupled into the first port fiber. Therefore, the optical circulator (103 and 105) enables a balanced output of the sample and reference beams to obtain accurate interference patterns from the OCT interferometer.

The output of the interferometer (interference patterns) is detected by the detector 121 (first detector). The first detector 121 is implemented as an array of photodiodes, a photo multiplier tube (PMT), a multi-array of cameras or other similar interference pattern detecting device. The signals output from the first detector 121 are pre-processed by data acquisition electronics (DAQ1) 131, and transferred to a computer 190. The computer 190 performs signal processing to generate OCT images in a known manner. The interference patterns are generated only when the path length of the sample arm matches the path length of the reference arm within the coherence length of the light source 110.

In the NIRAF/NIRF modality, an excitation light with a wavelength of 633 nm (radiation of second wavelength) from a second light source 810 irradiates the sample 170 through the PIU 150 and the distal optics of catheter 160.

The sample 170 emits autofluorescence (NIRAF signal) or fluorescence (NIRF signal) with broadband wavelengths of about 633 to 800 nm (radiation of third wavelength), in response to being irradiated by the excitation light. The auto-fluorescence (or fluorescence) light is collected by the distal optics of the catheter 160 and delivered to a third detector 833 (DET3) via an optical fiber 819 which connected to the PIU 150. The signal (fluorescence intensity signal) output from detector 833 is digitized by data acquisition electronics 132 (DAQ2) and transmitted to computer 190 for image processing.

The second detector 122 detects a part of the sample beam transmitted from the fiber coupler 108 via the multi-mode fiber 109. The second detector 122 outputs an analog signal corresponding to an intensity of the backscattered light (backscattered signal). The signal output from detector 122 is converted to digital data with data acquisition electronics (DAQ2) 132. Notably, as later explained more in detail, the digital signal corresponding to the intensity of the OCT backscattered light is used to calculate an angle at which the light of the OCT modality is incident on the sample. The intensity of the OCT backscattered light may also be used as a trigger signal for starting and/or ending pullback and image recording operations. Therefore, the signal output from detector 122, and converted to digital data by data acquisition electronics (DAQ2) 132 can be used directly as a trigger signal or it can be transferred to the computer 190 for control processing.

<Multimodality Probe>

Figure 2A:
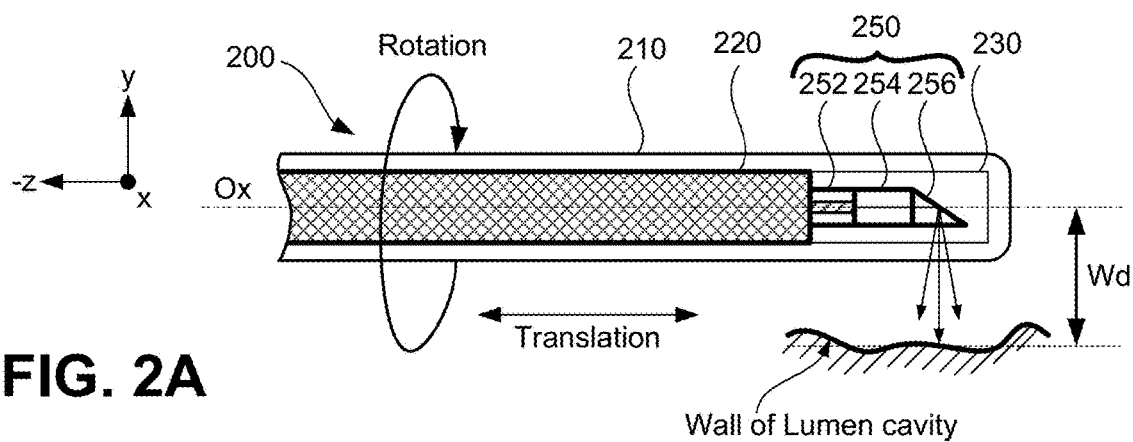
FIG. 2A illustrates an exemplary representation of an OCT-NIRAF probe (optical probe) usable in a catheter to image a sample.

FIG. 2A illustrates an exemplary representation of a distal end of catheter 160 (optical probe). As illustrated in FIG. 2A, a catheter 200 comprises a transparent sheath 210, a coil 220, a transparent protector 230 and an optical probe 250. The distal end of the probe 250 includes a double clad fiber (DCF) 252, a lens 254 (e.g., a GRIN lens or a ball lens), and a reflecting or diffracting surface 256. The catheter 200 is connected at the proximal end thereof to the PIU 150 (as shown in FIG. 1). The coil 220 delivers rotational torque from the proximal end to the distal end by a non-illustrated rotational motor located in the PIU 150. At the distal end of the probe 250, the reflecting surface or diffracting surface 256 (e.g., a mirror, a prism, or a grating) deflects the illumination light (sample beam) outward toward the sample (wall of the lumen cavity). As shown in FIG. 2A, the probe 250 is configured for side-view imaging, where the illumination light incident on the sample surface travels along a line transverse to the catheter's axis Ox. Here, since OCT and NIRAF data are obtained simultaneously, illumination light refers to light originated from OCT light source 110 and/or light emitted from NIRAF light source 810.

The coil 220 is fixed with the optical probe so that a distal tip (distal end) of the optical probe also spins (rotates) to obtain an omnidirectional view of the inner surface of hollow organs (lumens), such as vessels. At the proximal end of the optical probe 250 the double clad fiber 252 is connected with the PIU 150 via a non-illustrated fiber connector. The double clad fiber 252 is used to deliver and collect OCT light through the core, and to collect backscattered and fluorescent light from the sample through the cladding, as explained more in detail below. The lens 254 is used for focusing and collecting light to and/or from the sample, which is located at a working distance (Wd) from the center of the catheter. The intensity of backscattered light transmitted through the cladding of DCF 252 is relatively higher than the intensity of backscattered light collected through the core because the size of the core is much smaller than the cladding.

Figure 2B:
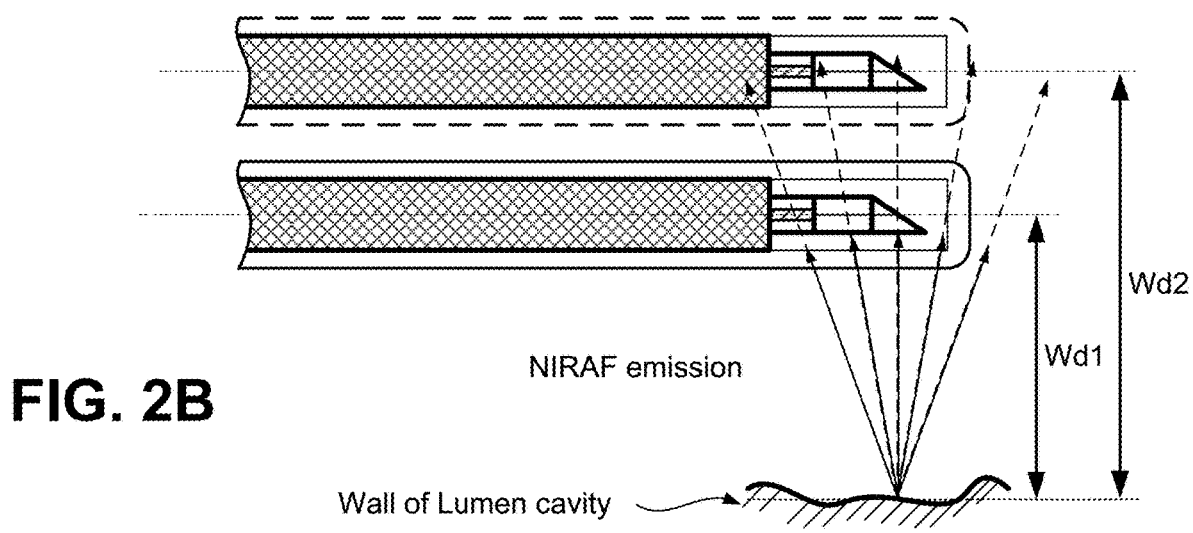
FIG. 2B illustrates variation of working distance of the multimodality probe and its effect on collecting NIRAF emission light.
Figure 2C:
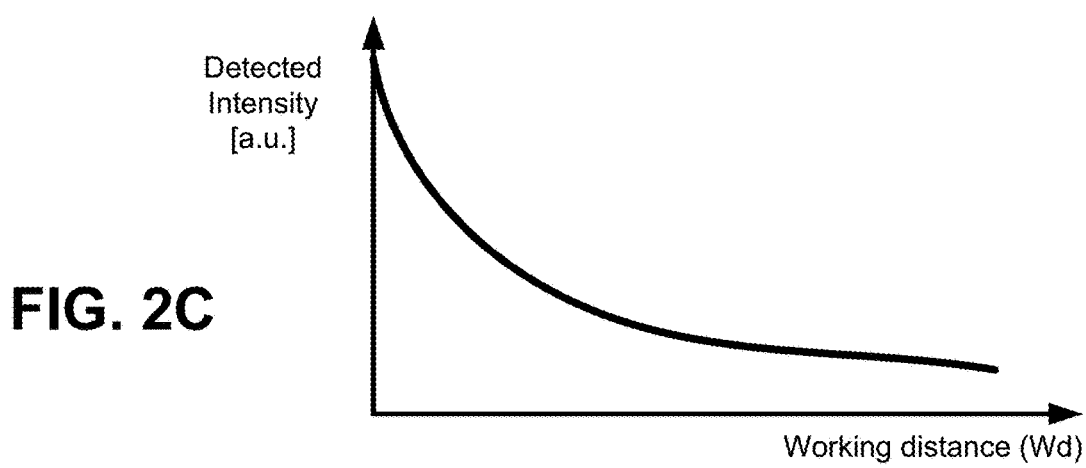
FIG. 2C is a graph illustrating a relationship of detected fluorescence intensity as a function of distance between catheter and the sample.

FIG. 2B illustrates the distal optics of catheter 200 imaging the wall of a lumen cavity (a blood vessel) at variable distances between the catheter and the sample surface (vessel wall). As illustrated in FIG. 2B, fluorescence and backscattered light can be collected at a plurality of working distances (Wd1, Wd2, Wd3 . . . ). Therefore, the detected fluorescence intensity is a function of the distance between catheter and the lumen cavity wall (wall of blood vessel sample). Accordingly, as illustrated in FIG. 2C, the detected intensity decreases with increased distance from sample (vessel wall) to catheter. Specifically, as shown in FIG. 2C, the shorter the working distance (Wd) is, the higher the detected intensity of the NIRAF/NIRF signal is because the collection efficiency of the catheter is generally higher at shorter distances. In addition, it has been noted by the inventors herein, that the intensity of the detected NIRAF/NIRF signal also depends on the angle at which the fluorescent light is collected.

<Angle Calculation>

The angle of interest in the NIRAF/NIRF modality is defined as the angle between the optical axis of the excitation light and the normal line to the sample surface (vessel wall). In other words, the detected NIRAF/NIRF intensity is dependent on the angle at which the excitation light is incident on the sample surface. However, because the OCT/NIRAF system operates in a 3D environment, a 3D angle must be considered. Specifically, the projections of light incident on the sample surface are more accurately observed when looking at the axial and transverse views of the blood vessel. Therefore, an axial angle is calculated using sequential readings as the distal optics is rotated; and a transverse angle is calculated using sequential readings along the pullback path for a fixed axial rotation angle.

Figure 3:
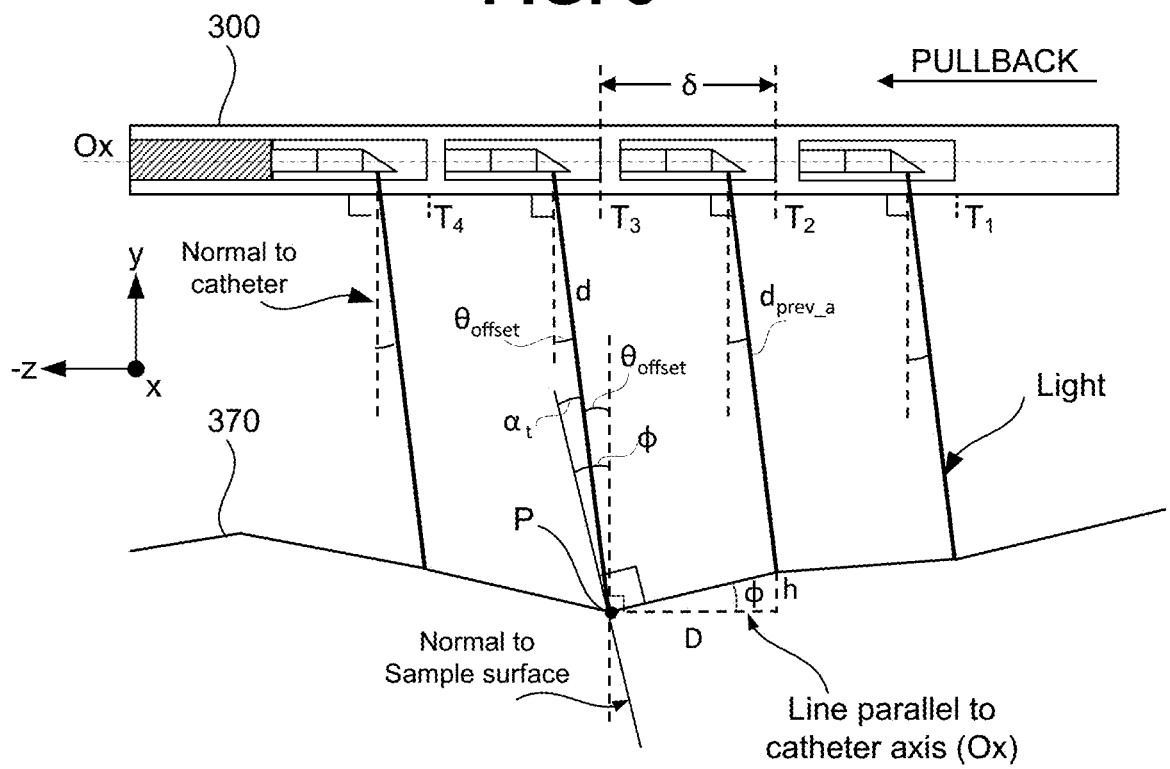
FIG. 3 illustrates a transverse view of distal optics (optical probe) of a catheter at sequential positions during a pullback operation.

FIG. 3 illustrates a transverse view of distal optics (optical probe) of the catheter 300 at sequential positions during a pullback operation. As explained above, OCT uses a helical scan and NIRAF/NIRF imaging is preformed simultaneously with the OCT scanning at the A-line scan rate of the OCT system. The diagram of FIG. 3 depicts positions (a plurality of transversal locations T1, T2, T3, T4) of the catheter 300 at corresponding timings t1, t2, t3, t4, along the pullback path, while scanning a sample 370 with a fixed (same) axial angle $\theta_a$.

In the transverse view shown in FIG. 3, the transverse angle $\alpha_t$ projected in the transverse plane of the sample is calculated using the following formulas defining Equation (1):

$$\alpha_t = |\varphi - \theta_{offset}| \qquad \text{Equation (1)}$$
$$= |\tan^{-1}(h/D) - \theta_{offset}|$$
$$= |\tan^{-1}((d - d_{prev\_a}) * \cos(\theta_{offset})/D) - \theta_{offset}|$$
$$= |\tan^{-1}((d - d_{prev\_a}) * \cos(\theta_{offset})/\delta) - \theta_{offset}|,$$

where:

$\varphi$ is the angle between the sample surface (blood vessel wall) and the catheter, at a point P where the light is incident on the sample surface;

$\theta_{offset}$ is the angle formed between the normal to the catheter and the direction (optical axis) at which the light from catheter propagates to the sample;

d is the current distance (at the offset angle) between the catheter and the sample surface (blood vessel wall);

$d_{prev\_a}$ is the previous distance between the catheter and the sample surface (blood vessel) measured at the same axial angle $\theta_a$, $\delta$ is the distance the catheter travels during pullback in between successive measurements (A-scans) at a fixed axial angle $\theta_a$;

D is the horizontal distance on the sample between consecutive adjacent measurements at a fixed axial angle $\theta_a$, and D is approximated as $\delta$; and h is the difference in vertical distance (working distance) between the current and previous measurement.

Accordingly, each of parameters "$\theta_{offset}$" and "h" used to define the transversal angle $\alpha_t$ can also be defined by the following equations:

$$\theta_{offset} = \tan^{-}(h/\delta) \quad \text{Equation (1a)}$$

$$h = (d - d_{prev\_a}) * \cos(\theta_{offset}) \quad \text{Equation (1b)}$$

Figure 4:
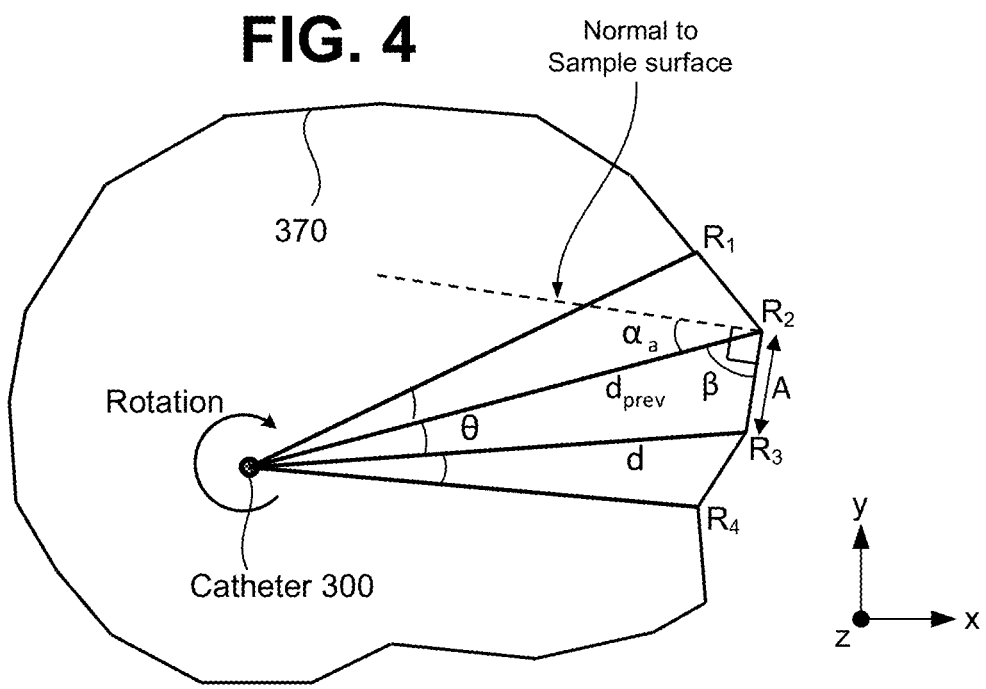
FIG. 4 illustrates an axial view of the distal end of the catheter with exemplary light rays incident on a blood vessel wall at a plurality of locations.

FIG. 4 illustrates an axial view of the distal end of catheter 300 with exemplary light rays incident on a blood vessel wall (sample 370) at a plurality of locations R1, R2, R3, R4 along a helical path. Measurements at each location are performed while scanning the sample 370 with a fixed (same) axial angle $\theta_a$. Each of locations R1, R2, R3, and R4 represents a different location on the sample surface at which a measurement is made while the catheter rotates. In FIG. 4, the angle projected in the axial plane (axial angle) $\alpha_a$ is calculated using the following formula Equation (2):

$$\alpha_a = |\pi/2 - \beta| \quad \text{Equation (2)}$$

where $\beta$, which is the angle between the optical axis (direction) of the excitation light and the sample surface (vessel wall), is defined as Equation (2a):

$$\beta = \sin^{-1}(d*\sin(\theta)/A) \quad \text{Equation (2a)}$$

where d is the current distance between the catheter and the sample surface (vessel wall); and A, which is a distance between successive rotational points (measurements) on the sample surface, is defined as Equation (2b)

$$A^2 = d_{prev}^2 + d^2 - 2d_{prev}*d\cos(\theta) \quad \text{Equation (2b).}$$

Accordingly, in the 3D environment, a 3D angle $\alpha$ is calculated using the projections of the angle of the incident light in both the transversal plane and the axial plane, as defined by the following formula Equation (3):

$$\alpha = \tan^{-1}[\text{sqrt}(\tan^2(\alpha_t) + \tan^2(\alpha_a))] \quad \text{Equation (3)}$$

Figure 5A:
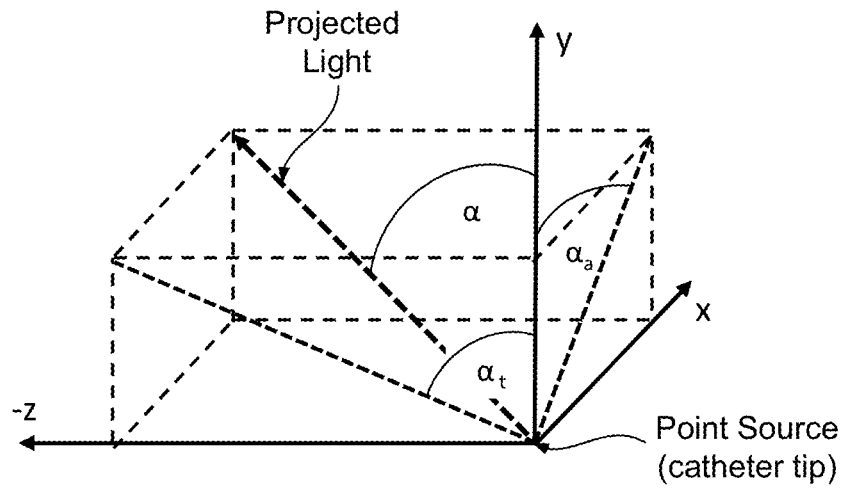
FIG. 5A illustrates a 3D environment of a light collection angle $\alpha$ defined as a result of including both an axial angle $\alpha_a$ and a transversal angle $\alpha_t$.

FIG. 5A illustrates the 3D environment of a light collection angle $\alpha$ defined as a result of considering both the axial angle $\alpha_a$ and the transversal angle $\alpha_t$. As illustrated in FIG. 5A, in a three dimensional space defined by x,y,z axes, the minus z direction (−z) represents the pullback direction of catheter 300, and the point where the 3 axes converge represents a point source (point light source) from which light is projected onto the sample and/or collected from the sample. From this point source, during a pullback operation, light is projected in the axial direction along the xy plane, and at the same time light is also projected in the transversal direction along the −zy plane. Therefore, it is advantageous to calculate the light projection/collection angle taking into consideration both the axial angle $\alpha_a$ and the transversal angle $\alpha_t$ of light incident on the sample.

Measured fluorescence intensity as a function of the angle $\alpha$ is obtained experimentally or by simulation. A calibration function is then calculated using the inverse of the intensity profile. For each angle input, the function outputs a calibration factor (a calibration value). The detected NIRAF/NIRF signal and OCT measurements are obtained during live simultaneous OCT and NIRAF imaging operation. The OCT measurements are used to calculate the angle between the optical axis (direction) of the excitation light and the normal line to the sample surface. The calibration factor is obtained by plugging-in the calculated angle into the calibration function. Then, multiplying the detected fluorescence signal by the calibration factor, a corrected fluorescence intensity is obtained in real-time.

Figure 5B:
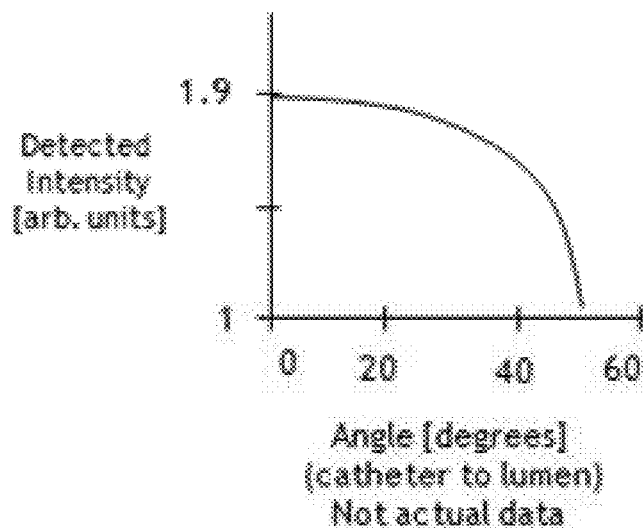
FIG. 5B illustrates an exemplary graph of detected fluorescence (NIRAF/NIRF) intensity profile as a function of the angle between the direction of excitation light and the normal to the sample surface.

FIG. 5B illustrates an exemplary graph of detected fluorescence (NIRAF/NIRF) intensity profile as a function of the angle of excitation light. The angle is defined as the space (measured in degrees) between the direction (optical axis) of excitation light incident on the sample and the normal to the point on the sample surface where the light is incident upon. As noted above, the angle between the direction (optical axis) of excitation light and the normal line of the sample surface includes the angle of excitation light projected both on the axial and transversal directions. The axial angle is calculated using sequential readings as the distal optics is rotated. The transverse angle is calculated using sequential readings along the pullback path for a fixed axial rotation angle.

The fluorescence signal intensity measured as a function of the angle between excitation light and sample surface serves to characterize the relationship between the NIRAF/NIRF intensity and the distance and angle from catheter to sample. In this regard, it should be noted that both the transversal angle defined by Equation (1) and the axial angle defined by Equation (2) take into consideration the distance (d) from catheter to sample of a current measurement as compared to the previous distance ($d_{prev}$) from catheter to sample of a previous measurement. That is, in calculating the transversal angle $\alpha_t$ and the axial angle $\alpha_a$, the current distance "d" is compared to the previous distance "$d_{prev}$", as shown in FIGS. 3 and 4. Accordingly, the calibration disclosed herein accounts for differences in working distance and differences in collection angle between multiple measurements, and adjusts the detected intensity accordingly therewith.

Figure 5C:
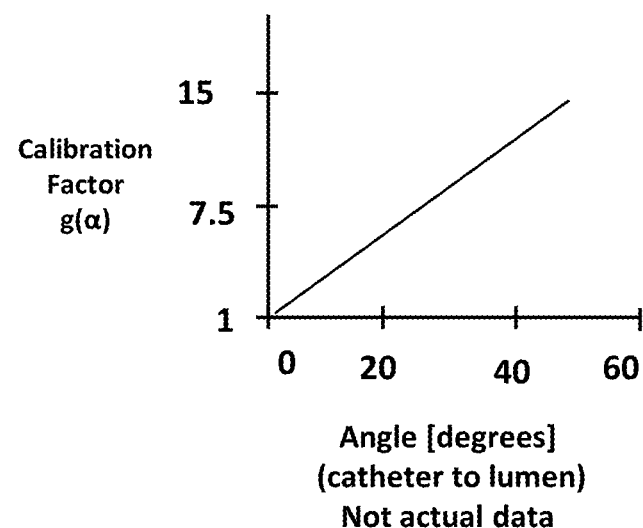
FIG. 5C illustrates an exemplary calibration function.

The intensity measurements obtained can be fitted using a linear or exponential function. Then the calibration function for angle (and distance) correction can be generated, as shown in FIG. 5C. FIG. 5C illustrates an exemplary NIRAF calibration function where for each angle $\alpha$ a calibration factor $g(\alpha)$ is obtained. After measuring the angle and distance from the catheter to the sample surface using the OCT image signals, the fluorescence signal intensity can be corrected by multiplying the calibration function values (a calibration factor) by the detected fluorescence signal. The calibration process is described below with reference to FIG. 8. The calibration curve, e.g., as shown in FIG. 5C, acts as a "lookup table" to determine what predefined calibration factor to use for a specific angle $\alpha$ obtained during live imaging. Once the fluorescence intensity detected is multiplied by the predetermined calibration factor $g(\alpha)$ to get the corrected intensity, the fluorescence signal has been calibrated for distance and angle of incidence of light. Therefore, the calibrated fluorescence signal can be used immediately to generate real-time highly accurate molecular images, or to generate co-registered OCT-fluorescence images.

Figure 6A:
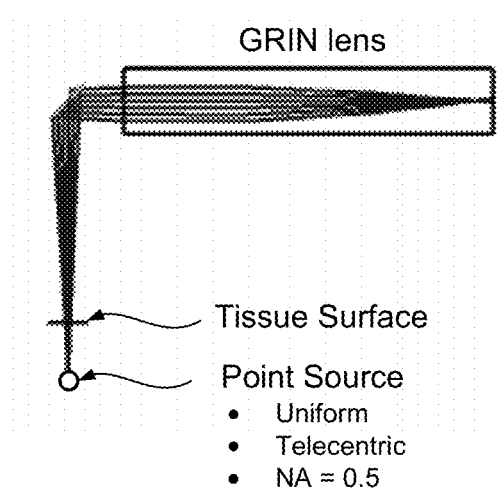
FIGS. 6A and 6B show simulated light propagation from a point source in tissue through an aperture into a GRIN lens as function of collection angle.
Figure 6B:
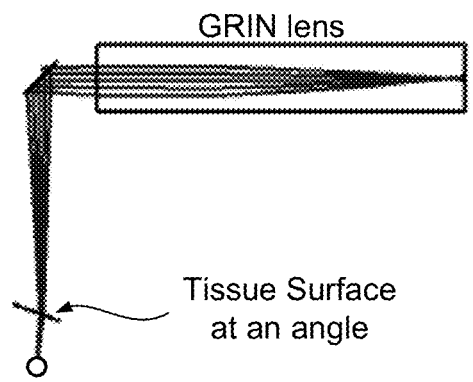
Figure 6C:
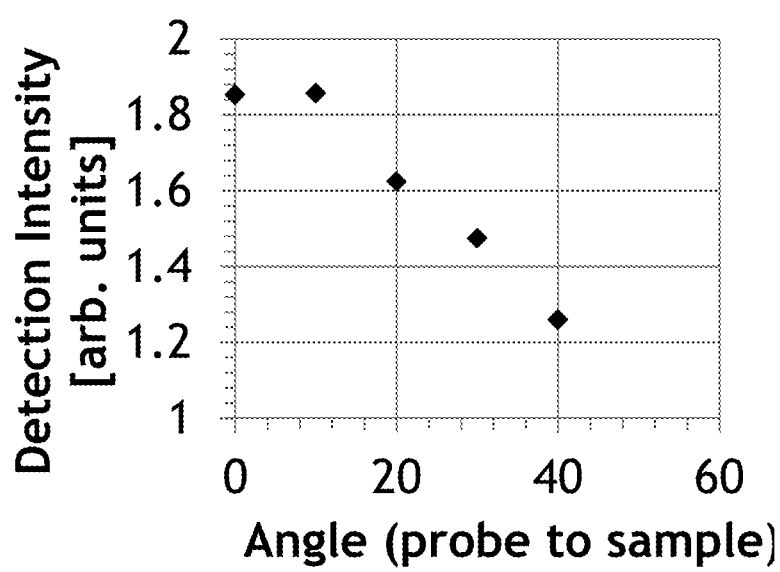
FIG. 6C illustrates exemplary detected intensity is a function of the collection angle being changed in steps of to degrees.

FIGS. 6A and 6B show simulated light propagation from a point source assumed to be inside the sample tissue and passing through an aperture (light spot size), and being directed into a GRIN lens as a function of the collection angle. In FIG. 6A, the point source is simulated to be uniform and is located at a position conjugate with the focusing point of the GRIN lens. In FIG. 6A, optical system is considered to have a numerical aperture (NA) of 0.5, and the system is considered to be telecentric. FIG. 6A simulates a situation where excitation light is incident on the sample along the normal to the sample surface. Now, turning to FIG. 6B, the same system is for simulating detection of light intensity originated from a point source within a tissue sample, but the angle of the point source in the tissue is changed. That is, in FIG. 6B, even if the point source is at a location conjugate with the focus point of the GRIN lens, the point source is not at a position normal to the light. The situation illustrated in FIG. 6B simulates a case where the excitation light is not incident along the normal to the sample surface. FIG. 6C illustrates simulated detected intensity is a function of the collection (or illumination) angle changed in steps of to degrees from a state shown in FIG. 6A to a state shown in FIG. 6B. FIG. 6C, therefore, shows that when the angle of light between the catheter and sample is considered (in addition to the distance), the detected intensity changes in a non-linear manner.

To calculate the angle between the optical axis (direction) of the excitation light and the normal line to the sample surface, the following angles are required:
(1) Axial rotation angle: given by motor encoder;
(2) Angle of propagation from catheter: given by optical design of the catheter's distal optics;
(3) Angle of sample surface in transverse view: to be calculated according to Equation (1); and
(4) Angle of sample surface in axial view: to be calculated according to Equation (2).

However, the angle calculation is not limited to calculating both the transverse and axial angles. NIRAF calibration can be achieved by calculating only one of the two angles (transverse or axial) and approximating the other (non-calculated) angle based on other data.

NIRAF calibration using only the axial angle can be achieved by setting the transverse angle to a constant value. To that end, one can approximate the transverse angle as being substantially equal to $\theta_{offset}$ ($\alpha_t=\theta_{offset}$), where $\theta_{offset}$ is the constant angle at which light from the catheter propagates towards the sample. This approximates the catheter as being substantially parallel to the surface of the sample (e.g., parallel to blood vessel) in the transverse view. Then, the 3D environment angle α can be calculated using the following formula Equation (4)

$$\alpha=\tan^{-1}[\text{sqrt}(\tan^2(\theta_{offset})+\tan^2(\alpha_a))] \quad \text{Equation (4)}$$

Alternatively, NIRAF calibration using only the transverse angle can be achieved by setting the axial angle to a constant value. To that end, one can approximate the axial angle $\alpha_a$ as being zero ($\alpha_a=0$). This approximates the blood vessel as being substantially circular in the axial view, with the catheter located at the center of a circle defining the axial view (cross section) of the blood vessel. This approximation could be used in the case of examining healthy blood vessels, where an assumption may be made that such blood vessels lack any significant amounts of plaque, for example. Therefore, in the case where the axial angle $\alpha_a$ is approximated as zero, the 3D environment angle α can be calculated using the following formula Equation (5).

$$\alpha=\tan^{-1}[\text{sqrt}(\tan^2(\alpha_t)+\tan^2(\alpha_a))] \quad \text{Equation (5)}$$

which means that Equation (5) becomes $\alpha=\alpha_t$.

Furthermore, enhanced NIRAF calibration can be achieved by sampling and/or averaging of the acquired data. In sampling, the data from each view (axial and transversal) can be sampled according to how much data is needed to obtain a reliable result. Alternatively, the data can be interpolated if more detail is necessary.

In averaging, several sets of data from the axial direction and/or transverse direction can be averaged to achieve better results. For instance, a moving average can be used to provide a smoother transition between successive pullbacks along the length of the vessel.

<Distance Calibration>

According to a second embodiment of the present disclosure, OCT data can be used to calibrate the detected NIRAF intensity as a function of distance, and the depth of signal and composition of tissue can be used to improve on the NIRAF signal compensated for distance variation. Specifically, in intravascular imaging, when blood is surrounded around the catheter's distal end, backscattering from blood cells is detected as a high-intensity signal with the second detector 122 (shown in FIG. 1). Then, when the blood cells are cleared by flushing media such as contrast agents, saline solution, and/or dextran, the signal received by the second detector 122 gradually drops off because the flushing media is relatively transparent, and because there is low backscattering due to lack scattering media (red blood cells) surrounding the distal end of the catheter.

According to the second embodiment, therefore, the intensity of the backscattered light detected by detector 122 is constantly monitored during blood clearance. Then, when the signal crosses a certain threshold, the computer 190 generates a trigger signal to automatically start pullback and to start recording both the OCT signal and the NIRAF/NIRF signal. In this manner, the NIRAF/NIRF signal can be recorded when the catheter is at a specific desired distance from the blood vessel wall. In addition, in a similar fashion to calibrating the NIRAF intensity using an angle intensity profile, the NIRAF signal can be calibrated for composition of tissue and depth of signal by obtaining from the OCT signal intensity profiles for varying depths of signal and composition of tissue, and defining a corresponding calibration function for each parameter.

<IVUS System>

Moreover, intravascular ultrasound (IVUS) can be used instead of OCT to calibrate the NIRAF signal for distance, angle, depth, and composition of tissue. IVUS has been widely used for assessing tissue properties within the vessel wall through IVUS elastography and histology techniques. Indeed, various related disclosures have already described certain combined NIRF-IVUS systems where the catheter to vessel wall distance is estimated from IVUS data and the estimated distance is incorporated into a light propagation model (based on Beers' Law) to correct NIRF measurements for variable sensing distances. However, no related art has described the novel concept of including both the transverse and axial angles, in addition to the working distance, into a calibrating function to correct the intensity of NIRAF/NIRF signals.

Accordingly, in the present application, IVUS and/or OCT data corresponding to depth and composition of tissue can be combined with the angle measurements described above to calibrate the intensity of NIRAF/NIRF signals. Specifically, as previously mentioned, IVUS is capable of assessing tissue properties within the vessel wall through elastography and virtual histology techniques, but is limited in terms of image resolution. On the other hand, OCT can evaluate clinically important plaque structural features such as the thickness of fibrous caps and the presence of a necrotic core or lipid deposits at a resolution of 10 to 15 µm, which is approximately five times better than 40 MHz IVUS. Therefore, depending on the level of desired resolution, OCT or IVUS data corresponding to depth and composition of tissue can be selectively combined with the angle measurements described above to calibrate the intensity of NIRAF/NIRF signals. It should be noted, however, that although using IVUS (instead of OCT) to measure depth and composition of tissue can be done without blood clearing, the IVUS measurement focuses mainly on blood surrounding the catheter rather than the vessel wall tissue itself.

<System Control and Image Processing>

Figure 7:
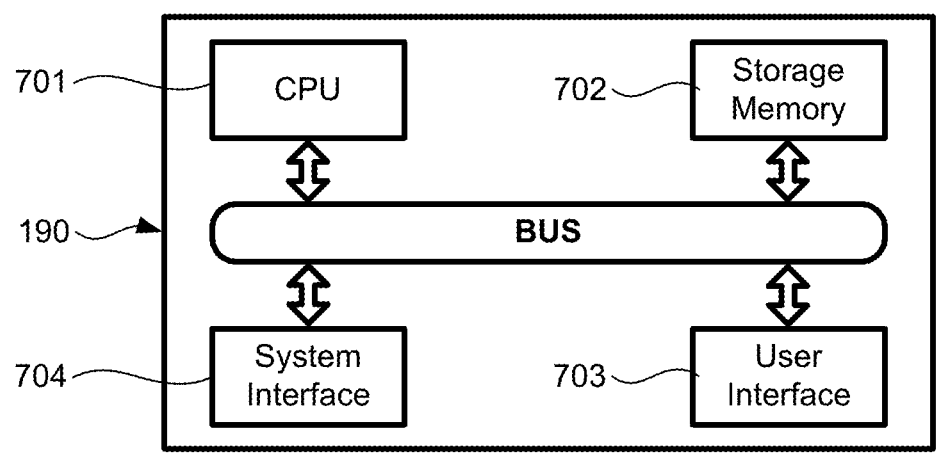
FIG. 7 is a block diagram of an exemplary computer control system for performing control and image processing in the multimodality OCT-NIRAF system.

FIG. 7 is a schematic diagram of an exemplary computer control system for the OCT/NIRAF system 100. As shown in FIG. 7, the computer control system is representative of computer 190 shown in FIG. 1. In FIG. 7, the computer 190 includes a central processing unit (CPU) 701, a storage memory (ROM/RAM) 702, a user input/output (I/O) interface 703, and a system interface 704. The various components of the computer 190 communicate with each other via a data bus (BUS) in a known manner.

Storage memory 702 includes one or more computer-readable and/or writable media, and may include, for example, a magnetic disc (e.g., a hard disk drive HHD), an optical disc (e.g., a DVD®, a Blu-ray®, or the line), a magneto-optical disk, semiconductor memory (e.g., a non-volatile memory card, Flash® memory, a solid state drive, SRAM, DRAM), an EPROM, an EEPROM, etc. Storage memory 702 may store computer-readable data and/or computer-executable instructions including Operating System (OS) programs, and control and processing programs.

The user interface 703 provides a communication interface (electronic connections) to input/output (I/O) devices, which may include a keyboard, a display (LCD or CRT), a mouse, a printing device, a touch screen, a light pen, an external optical storage device, a scanner, a microphone, a camera, a drive, communication cable and a network (either wired or wireless).

The system interface 704 also provides communication interfaces (electronic connections) for one or more of the light source 110, detectors 121-122 and 833, data acquisition electronics DAQ1 (131) and DAQ (132), and the patient unit interface (PIU) 150. The system interface 704 may include programmable logic for use with a programmable logic device (PDL), such as a Field Programmable Gate Array (FPGA) or other PLD, discrete components, integrated circuitry (e.g., an Application Specific Integrated Circuit (ASIC)), or any other components including any combination thereof.

The function of the user interface 703 and of the system interface 704 may be realized at least in part by computer executable instructions (e.g., one or more programs) recorded in storage 702. Moreover, the computer 190 may comprise one or more additional devices, for example, components such as a communications or network interface, a circuit interface (e.g., a field-programmable gate array: FPGA) to control one or more of the light sources 110 and 810, detectors 121-122 and 833, mirror 140, and PIU 150.

The CPU 701 is comprised of one or more processors (e.g., a microprocessor, microcontroller, digital signal processor) configured to read and execute computer-executable instructions stored in the storage memory 702. The computer-executable instructions may include those for the performance of the novel processes, methods and/or calculations disclosed herein. For example, CPU 701 calculates the intensity backscattered light based on electric signals output from optical detectors 120 (121-122) and pre-processed by the acquisition electronics 130, and using the OCT signals CPU 701 can calculate the catheter wording distance and the axial and transversal angles. In addition, CPU 190 calculates and/or determines intensity of the NIRAF signals and performs correction of the NIRAF signals, as described more in detail elsewhere in this disclosure.

Figure 8:
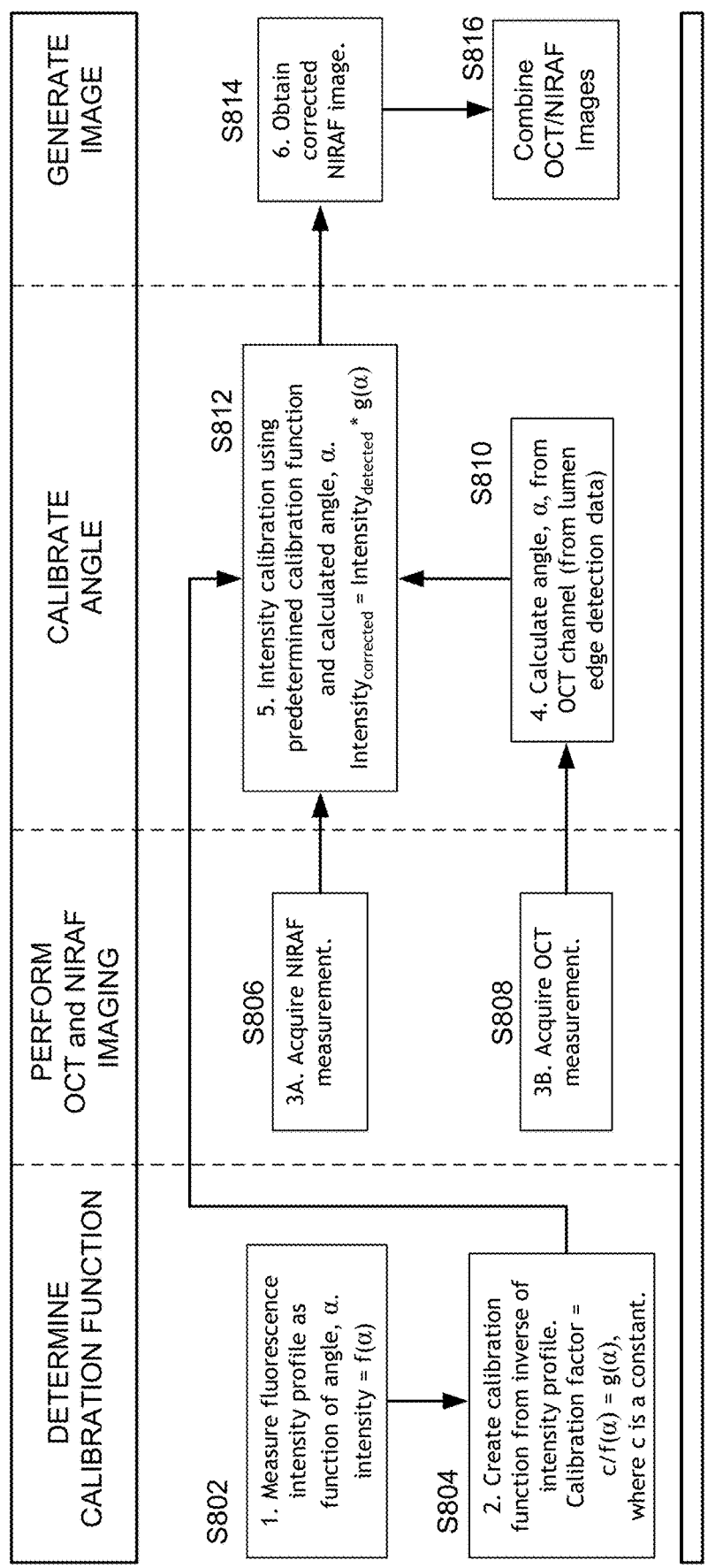
FIG. 8 illustrates an exemplary flow process for controlling the multimodality system to perform angle calibration and image generation.
Figure 9A:
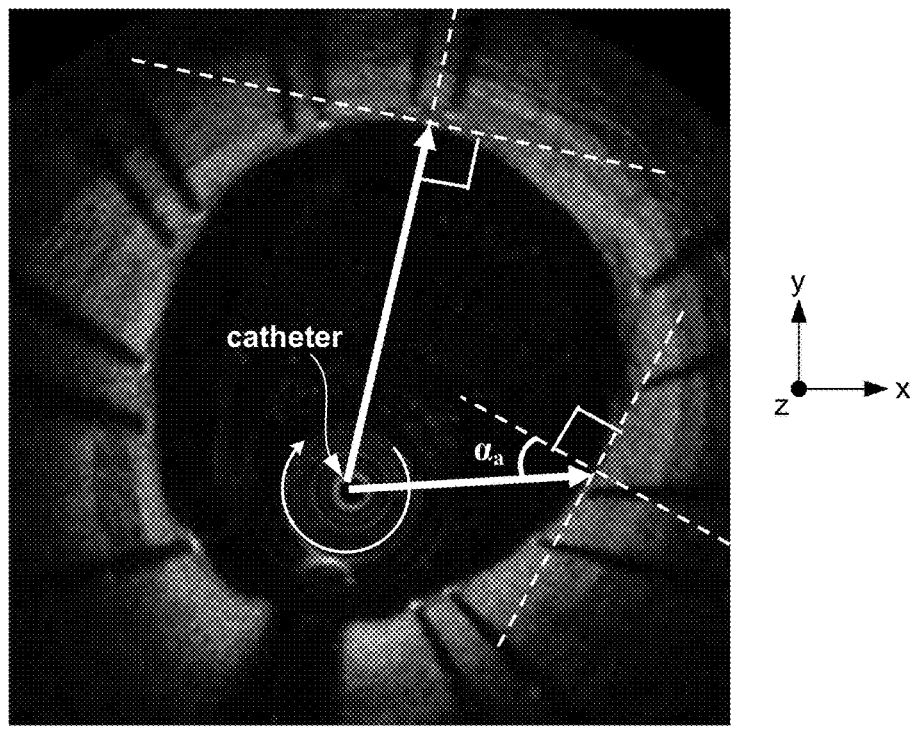
FIG. 9A shows an exemplary axial image and FIG. 9B shows an exemplary transversal image of a bodily lumen acquired using the multimodality system.
Figure 9B:
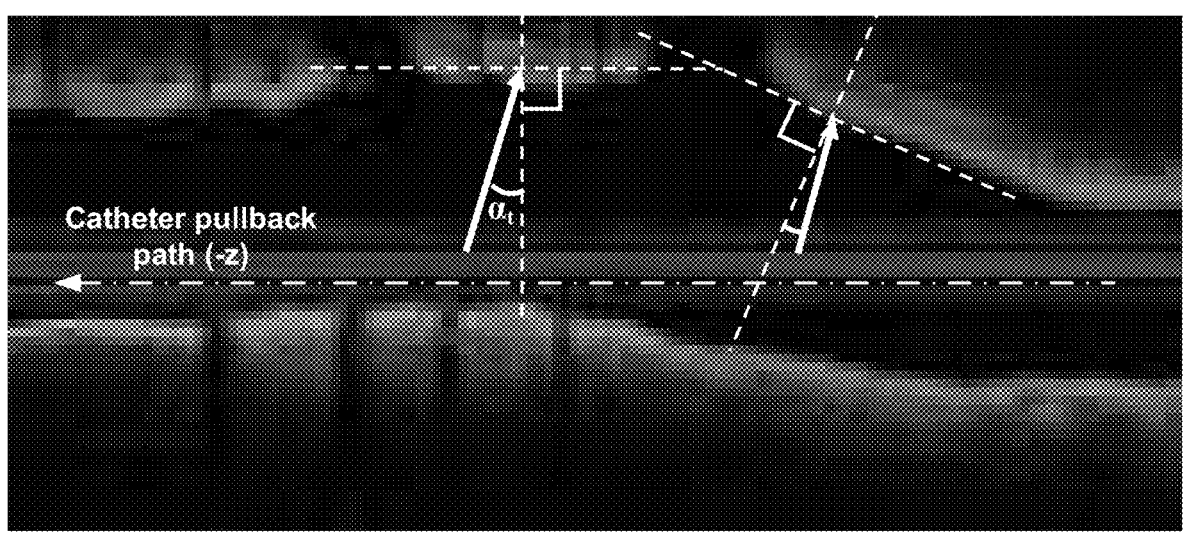

FIG. 8 illustrates an exemplary flow process for controlling the OCT/NIRAF system to perform angle calibration during simultaneous OCT and NIRAF imaging. The process of FIG. 8 assumes an operational state in which a non-illustrated system console including computer 190 undergoes a system setup. System console setup may include, for example, executing a booting sequence of computer 190 and initializing the system software that operates the OCT/NIRAF system 100. In addition, system setup may include, at steps S802-S804, the computer 190 establishing a predetermined calibration function, or accessing a predetermined calibration function already established and stored in a non-illustrated data storage memory.

Specifically, at step S802, the computer 190 controls the OCT/NIRAF system 100 to measure a fluorescence intensity profile as a function of light propagation angle α [intensity=f(α)]. At step S804, the computer 190 uses the fluorescence intensity profile to create a calibration function from the inverse of the intensity profile. The inverse of the intensity profile becomes a calibration factor, $g(\alpha)=c/f(\alpha)$, where c is a scalar constant (e.g., a base line). The process of steps S802-S804 to establish a predefined calibration function and obtain a calibration factor can be performed in advance of any live imaging.

Subsequent to establishing a predetermined calibration function, computer 190 controls the OCT/NIRAF system 100 to simultaneously acquire OCT measurement data and NIRAF measurement data, at steps S806 and S808, respectively. At step S810, computer 190 calculates angle α according to one or more of Equations (1)-(4). At step S812, computer 190 performs adjustment of the NIRAF intensity signal using the predetermined calibration function and the calculated angle. Adjustment (calibration) of NIRAF intensity signal is performed using the following formula Equation (6):

$$\text{Intensity}_{corrected} = \text{Intensity}_{detected} * g(\alpha) \qquad \text{Equation (6)},$$

where $g(\alpha)=c/f(\alpha)$.

After obtaining the intensity corrected NIRAF/NIRF signal, the flow process advances to step S814 where CPU 701 performs image processing to obtain a corrected NIRAF image. Subsequently at step S815 the computer 190 can also obtain a composite 3D image by combining the corrected NIRAF image with OCT images acquired at various depths of the tissue sample. The results of the process shown in FIG. 8 can be output from computer 190 via user interface 703 (shown in FIG. 7).

<Pullback Operation Using FORJ>

Figure 10A:
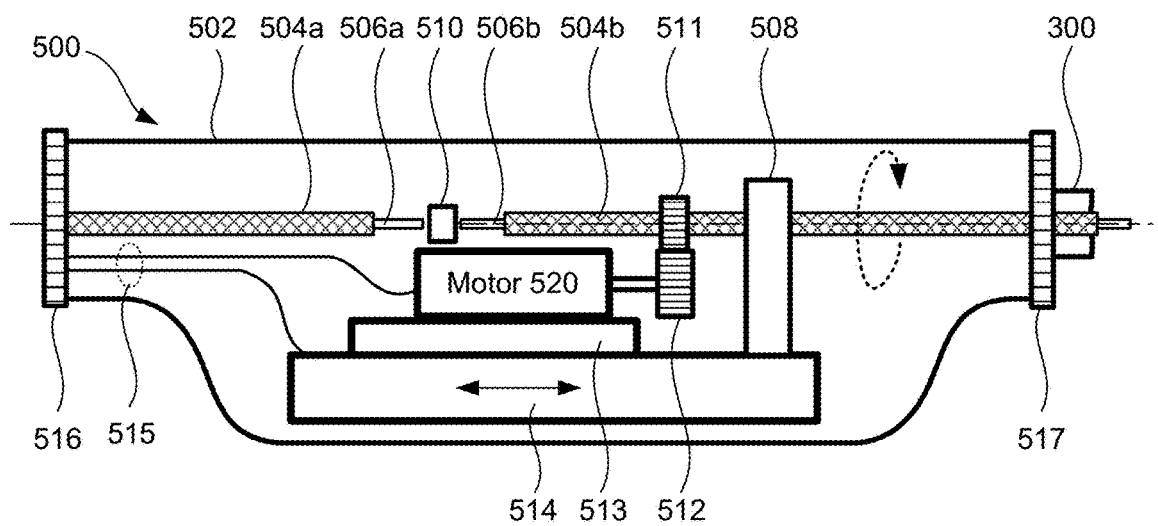
FIG. 10A schematically shows one exemplary implementation of relevant parts of a patient interface unit (PIU).
Figure 10B:
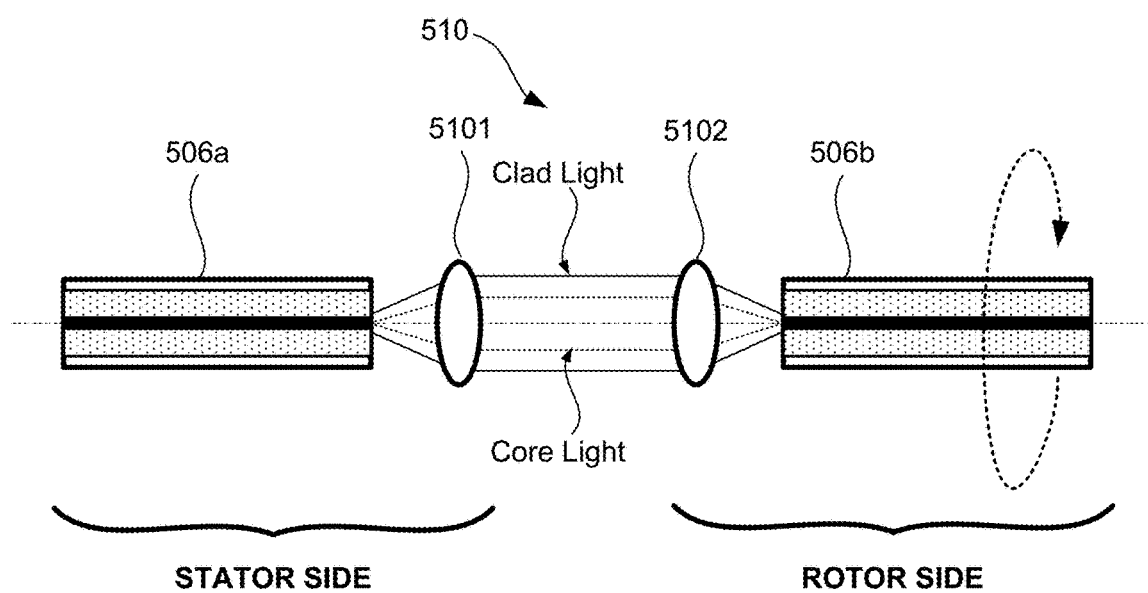
FIG. 10B shows an exemplary implementation of free-space optics used as optical connections in a fiber optic rotary joint (FORJ).

FIG. 10A schematically shows one exemplary implementation of relevant parts of a patient interface unit (PIU) 500 which is located at the proximal end of catheter 300 (shown in FIG. 1). As shown in FIG. 10A, the PIU 500 is encased in an outer housing 502, which serves as a housing for mechanical, electronic, and optical components useful for control of the optical probe. Also included in the housing 502 is a fiber optic rotary joint (FORJ) comprised of a rotational motor 520, a motorized translation stage 514, and free-space optical connections 510. At one end, the PIU 500 is provided with an optical/electrical connector 516, and at the other end thereof the PIU 500 is provided with an optical connector 518. A double clad fiber 506a encased in a sheath 504a and electronic wiring connections 515 connect the PIU 500 to computer 190 via the connector 516. A double clad fiber 506b encased in a sheath 504b are part of the catheter 300 and are connected to the PIU 500 via a connector 517. It is understood that other elements such as a guidewire and one or more conduits, e.g., for delivering a blood clearing medium (liquid), can be included in the catheter 300. In addition, although a single DCF 506a and a single DCF 506b are shown, more than one fiber can be used to transmit the light from OCT light source 110 and from light from NIRAF light source 810.

The motor 520 and motorized translation stage 514 provide rotational and translational torque for actuation of the movable components of catheter 300. Motor 520 drives a non-labeled shaft to rotate a gear 512 which transfers rotational torque to gear 511. The motor 520 is mechanically fixed to a base plate 513. In addition, a motorized translation stage 514 is also fixed to the base plate 513. The motorized translation stage 514 serves to provide translational torque for controlling linear movement (insertion into a lumen or pullback) of the movable components within catheter 300. A support 508 provides support and directional control for translational movement of the movable components within catheter 300. In other words, support 508 serves as a linear guide for translational movement. The motorized translation stage 514 is also used for providing translational torque during pullback. The connector 517 is a catheter connector to be connected to the catheter 300.

Rotational and translational torque for actuation of the movable components of catheter 300 is not limited to motorized movement. Instead of motors and mechanical gears, rotational and translational torque may also be implemented by using pneumatic or electromagnetic driving mechanisms to achieve rotary and forward/backward mechanical movement. See, for example, publication US 20140180133 (Brennan et al.), which is incorporated by reference herein in its entirety. In addition, ultrasonic motor (USM) systems may be advantageously used, for example, in a case where the optical probe is under the magnetic field of an MR-based modality, USM or pneumatic drive mechanisms can be used in the FORJ to avoid the effects that a magnetic field would have on metallic based driving mechanisms.

FIG. 5B shows a detailed view of an exemplary implementation of the catheter free-space optical connections 510 which are part of the FORJ. The catheter optical connections 510 include free space optics such as a pair of lenses 5101 and 5102. The FORJ allows uninterrupted transmission of an optical signal while rotating the double clad fiber on the right side (rotor side) along the fiber axis. The FORJ has a free space optical beam coupler to separate rotor and stator sides. The rotor and stator sides both comprise a double clad fiber 506 with a lens to ensure the light is transmitted as a collimated beam. The rotor side is connected to the catheter 300, and the stator side is connected to the optical subsystems within the PIU 500. The rotational motor 520 delivers the torque to the rotor or rotational side. It should be understood from FIG. 5B, that the lens 5101 needs not be separated from DCF 506a, and similarly lens 5102 needs not be separated from DCF 506b, as long as a collimated beam is transferred from the stator side to the rotor side and vice versa the lenses can be arranged at anywhere between DCF 506a and DCF 506b.

<Multi-Channel Catheter>

Figure 11A:
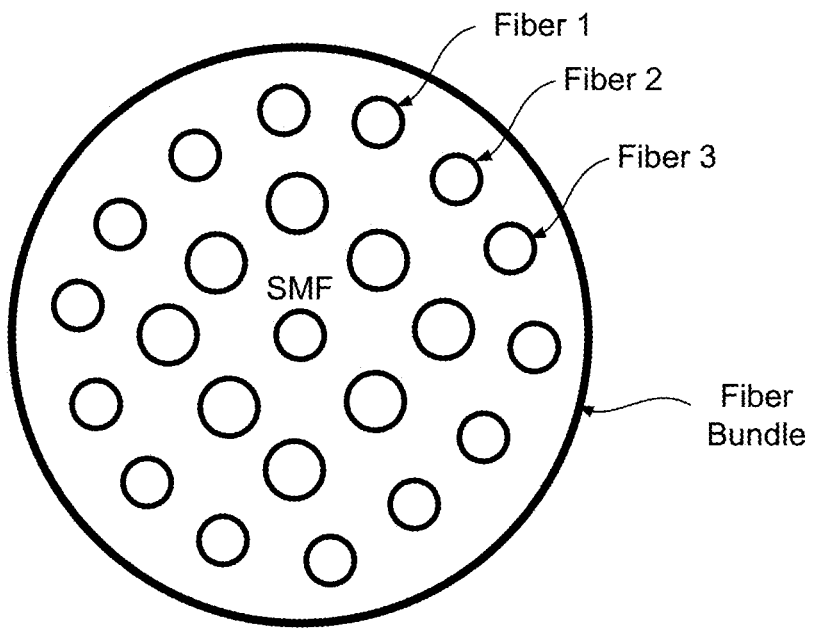
FIG. 11A shows a cross-sectional view of an exemplary fiber bundle, and FIG. 11B show the cross-section of a multi-fiber structure.
Figure 11B:
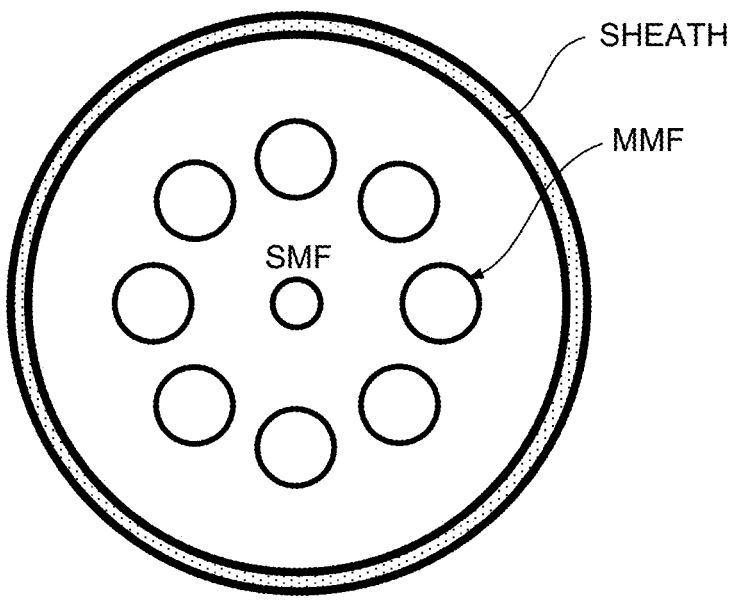

As described above, the catheter 300 includes a single double clad fiber (DCF) for delivering and collecting both OCT light and NIRAF/NIRF light. However, the catheter can be modified to include a fiber bundle, a holey fiber (a photonic crystal microstructure fiber), or a custom-made multi-fiber structure. FIG. 11A shows a cross-sectional view of an exemplary fiber bundle, and FIG. 11B show a multi-fiber structure. In both FIGS. 11A and 11B, a center fiber is a single mode fiber (SMF) used for transmitting the OCT light, while the other fibers surrounding the center fiber are multimode fibers (MMF) or single mode fibers which can be used for transmitting NIRAF light.

While the present patent application has been described with reference to exemplary embodiments, it is to be understood that the invention is not limited to the disclosed exemplary embodiments. The scope of the following claims is to be accorded the broadest interpretation so as to encompass all possible modifications and equivalent structures and functions. To that end, it must be noted that the terminology used herein is for the purpose of describing particular embodiments only and is not intended to be limiting.

As used herein, when referring to a light of, for example, a first, second or third wavelength, this may refer to a single wavelength (e.g., 1033 nm) or a wavelength band (e.g., ranging from 633 to 800 nm).

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated.

It should be further noted that operations performed as method steps/processes or otherwise described herein in algorithm form are those operations requiring physical manipulations of physical quantities, which usually but not necessarily, take the form of electrical or magnetic signals capable of being stored, transferred, combined, transformed, compared, and otherwise manipulated electronically. Therefore, unless specifically stated otherwise, it will be apparent to those skilled in the art that throughout the above description, discussions utilizing terms such as "processing" or "computing" or "displaying" or "calculating" or "comparing, "calibrating" "generating" or "determining" and the like, refer to the action and processes of a computer system, or similar electronic component, that manipulates and transforms data represented as physical (electronic) quantities within the computer system's registers and memories into other data similarly represented as physical quantities within the computer system memories or registers or other such information storage, transmission, or display device.

LIST OF EXEMPLARY REFERENCES

The following non-patent literature (NPL) and patent publications, which are considered "nonessential material", are hereby incorporated by reference herein in their entirety:

1. H. Wang, J. A. Gardecki, G. J. Ughi, P. V. Jacques, E. Hamidi, G. J. Tearney, "Ex vivo catheter-based imaging of coronary atherosclerosis using multimodality OCT and NIRAF excited at 633 nm," Biomedical Optics Express 6(4), 1363-1375 (2015);
2. G. J. Ughi, J. Verjans, A. M. Fard, H. Wang, E. Osborn. T. Hara, A. Mauskapf, F. A. Jaffer, and G. J. Tearney, "Dual modality intravascular optical coherence tomography (OCT) and near-infrared fluorescence (NIRF) imaging: a fully automated algorithm for the distance-calibration of NIRF signal intensity for quantitative molecular imaging," Int. J. Cardiovasc. Imagine 31, 259-268 (2014);

3. S. Liu, J. Eggermont, Ron Wolterbeek, A. Broersen, C. A. G. R. Busk, H. Precht, B. P. F. Lelieveldt, J. Dijkstra, "Analysis and compensation for the effect of the catheter position on image intensities in intravascular optical coherence tomography," J. Biomed. Opt. 21(12) (2016);
4. A J Dixon, J A Hossack, "Intravascular near-infrared fluorescence catheter with ultrasound guidance and blood attenuation correction", Journal of Biomedical Optics. 2013; 18(5):056009. doi:10.1117/1.JBO.18.5.056009.
5. Hao Wang, "Near infrared autofluorescence augmentation of optical coherence tomography for diagnosis of coronary atherosclerosis", Thesis/Dissertation, Boston University, 2014;
6. Patent publications include: WO20212039679, US20160038029, WO2016015052, US20160228097, US 20140180133, JP2006194812, EP2846149, WO2016036314, U.S. Pat. Nos. 8,190,241, 9,557,154.

What is claimed is:

1. An apparatus, comprising:
   a catheter extending from a proximal end to a distal end along a catheter axis, the catheter configured to simultaneously direct a radiation of first wavelength and a radiation of second wavelength from its distal end thereof as a light beam transverse to the catheter axis, and configured to simultaneously collect at its distal end thereof, from a plurality of locations of the sample, backscattered radiation of first wavelength in response to irradiation with the radiation of first wavelength and a radiation of third wavelength emitted in response to irradiation with the radiation of second wavelength;
   a first detector and a second detector operatively coupled to the catheter, the first detector configured to detect an intensity of the radiation of third wavelength and the second detector configured to detect an intensity of the backscattered radiation of first wavelength collected by the catheter from each of the plurality of locations of the sample; and
   a processor operatively coupled to the first detector and the second detector, and configured to:
   acquire data from the first detector about the intensity of the radiation of third wavelength and data from the second detector about the intensity of the backscattered radiation of first wavelength,
   based on the data about the intensity of the backscattered radiation of first wavelength, calculate an angle α at which the radiation of second wavelength is incident on each of the plurality of locations of the sample,
   adjust the intensity of the radiation of third wavelength detected by the first detector, using a calibration factor g(α), and
   generate an image using data corresponding to the adjusted intensity of the radiation of third wavelength,
   wherein the calibration factor g(α) is a function of the angle α calculated for each of the plurality of locations,
   wherein the processor adjusts the intensity of the radiation of third wavelength by multiplying the detected intensity of the radiation of third wavelength by the calibration factor g(α) obtained from the backscattered radiation of first wavelength at each of the plurality of locations,
   wherein the processor calculates the angle α by combining values of an axial rotation angle $\alpha_a$ measured along an axial plane of the sample, and a transversal angle $\alpha_t$ measured along a transversal plane of the sample,
   wherein the axial plane is perpendicular to the catheter axis and the transversal plane is parallel to the catheter axis, and
   wherein the transversal angle $\alpha_t$ is measured along the transversal plane of the sample between a line normal to the sample surface and the light beam transverse to the catheter axis along which the radiation is directed from the catheter to the sample, and the axial rotation angle $\alpha_a$ is measured along the axial plane of the sample between a line normal to the sample surface and the light beam transverse to the catheter axis along which the radiation is directed from the catheter to sample.

2. The apparatus according to claim 1, further comprising;
   a patient interface unit (PIU) operatively connected to the proximal end of catheter,
   wherein the PIU includes a fiber optic rotary joint (FORA a rotational motor and translation stage,
   wherein the catheter includes a double clad fiber and a coil disposed in a protective sheath,
   wherein the FORJ is configured to provide uninterrupted transmission of the radiation of first wavelength and the radiation of second wavelength from one or more light sources to the catheter and transmission of the collected radiation of third wavelength and backscattered radiation of first wavelength respectively to the first detector and the second detector while rotating the double clad fiber within the catheter during a pullback operation.

3. The apparatus according to claim 2,
   wherein the processor calculates the transversal angle $\alpha_t$ using sequential readings of the backscattered radiation of first wavelength backscattered from the plurality of locations and detected by the second detector along a pullback path of the catheter without changing the axial rotation angle, and
   wherein the processor calculates the axial rotation angle $\alpha_a$ using sequential readings of the backscattered radiation of first wavelength backscattered from the plurality of locations and detected by the second detector as the catheter is simultaneously rotated and pulled back.

4. The apparatus according to claim 1,
   wherein the processor calculates the angle α using the following formula $$\alpha = \tan^{-1}[\text{sqrt}(\tan^2(\theta_{offset}) + \tan^2(\alpha_a))]$$

where
   $\alpha_t$ is the transversal angle between the line normal to the sample surface and the light beam transverse to the catheter axis projected on the plane parallel to the catheter axis, and $\alpha_a$ is the axial rotation angle between the line normal to the sample surface and the light beam transverse to the catheter axis projected on the plane perpendicular to the catheter axis,
   the transversal angle $\alpha_t$ is calculated using sequential readings of the backscattered radiation of first wavelength backscattered from at least two transversal locations of the sample detected by the second detector along a pullback path of the catheter while the axial rotation angle is fixed, and
   the axial rotation angle $\alpha_a$ is calculated using sequential readings of the backscattered radiation of first wavelength backscattered from at least two rotational locations detected by the second detector as the catheter is simultaneously rotated and pulled back.

5. The apparatus according to claim 1,
wherein the processor further calculates the angle α using the following formula $$\alpha = \tan^{-1}[\sqrt{\tan^2(\theta_{offset}) + \tan^2(\alpha_a)}]$$

where
$\theta_{offset}$ is an angle formed between the line normal to the catheter and the light beam transverse to the catheter axis projected on the plane parallel to the catheter axis, and
$\alpha_a$ is the axial rotation angle between the line normal to the sample surface and the light beam transverse to the catheter axis projected on the plane perpendicular to the catheter axis,
the axial rotation angle $\alpha_a$ is calculated using sequential readings of the backscattered radiation of first wavelength backscattered from at least two rotational locations and detected by the second detector as the catheter is simultaneously rotated and pulled back.

6. The apparatus according to claim 1,
wherein the processor further calculates the angle α using the following formula $$\alpha = \alpha_t$$

where
$\alpha_t$ is the transversal angle between the line normal to the sample surface and the light beam transverse to the catheter axis projected on the plane parallel to the catheter axis, and
the transversal angle $\alpha_t$ is calculated using sequential readings of the backscattered radiation of first wavelength backscattered from the plurality of locations and detected by the second detector from along a pullback path of the catheter.

7. The apparatus according to claim 4,
wherein the sample is a bodily lumen, and
wherein the processor calculates the transversal angle $\alpha_t$ using the following formulas:

$$\alpha_t = |\varphi - \theta_{offset}|, \alpha_t = |\tan^{-1}(h/D) - \theta_{offset}|, \alpha_t = |\tan^{-1}((d - d_{prev\_a})\cos(\theta_{offset})/D) - \theta_{offset}|, \alpha_t = |\tan^{-1}((d - d_{prev\_a})\cos(\theta_{offset})/\delta) - \theta_{offset}|,$$

where
φ is an angle formed between the lumen surface and a line parallel to the catheter axis at a current measurement location,
$\theta_{offset}$ is an angle formed between the line normal to the catheter and the light beam transverse to the catheter axis,
d is a current distance between the catheter and the lumen surface measured at the angle $\theta_{offset}$ at the current measurement location,
$d_{prev\_a}$ is a previous distance between the catheter and the lumen surface measured at the angle $\theta_{offset}$ at a previous measurement location,
δ is a distance that the catheter travels along the pullback path in between two consecutive measurement locations,
D is a distance on the lumen surface between the two consecutive measurement locations, and
h is a difference in distance from the catheter to the lumen surface between the current measurement location and the previous measurement location.

8. The apparatus according to claim 7,
wherein the processor calculates the axial rotation angle $\alpha_a$ using the following formulas:

$$\alpha_a = |\pi/2 - \beta|$$

where β, which is an angle formed between the light beam transverse to the catheter axis and the lumen surface, is defined as $$\beta = \sin^{-1}(d^* \sin(\theta)/A)$$

A, which is a rotational distance on the lumen surface between two consecutive rotational measurement locations, is defined as $$A^2 = d_{prev}^2 + d^2 - 2 d_{prev}^* d \cos(\theta),$$

where d is a distance of an optical path from the distal end of the catheter to the lumen surface at a current rotational measurement location, $d_{prev}$ a distance of an optical path from the distal end of the catheter to the lumen surface at a previous rotational measurement location, and θ is an angle between d and $d_{prev}$.

9. The apparatus according to claim 1, further comprising:
a swept source laser configured to emit the radiation of first wavelength having a wavelength of 1310 nm+/−50 nm; and
an excitation light source configured to emit the radiation of second wavelength having a center wavelength of 633 nm,
wherein the radiation of third wavelength is either near-infrared autofluorescence (NIRAF) or near-infrared fluorescence (NIRF) emitted by the sample in response to being irradiated with the radiation of second wavelength.

10. The apparatus according to claim 9, further comprising:
distal optics arranged at the distal end of the catheter, the distal optics including a double clad fiber with a ball lens or a GRIN lens at the tip thereof configured for side-view imaging,
wherein the processor is further configured to obtain from the plurality of locations of the sample optical coherence tomography (OCT) data and either NIRAF or NIRF data simultaneously through the catheter.

11. The apparatus according to claim 1,
wherein the radiation of first wavelength has a wavelength of 1310 nm+/−50 nm, and the radiation of second wavelength has a center wavelength of 633 nm,
wherein the radiation of third wavelength includes fluorescent light emitted by the sample in response to irradiation thereof with the radiation of second wavelength, and
wherein the backscattered radiation of first wavelength is low-coherence light backscattered from the sample in response to irradiation thereof with the radiation of first wavelength.

12. A method, comprising:
transmitting radiation of at least three different wavelengths via a catheter having a proximal end and a distal end arranged along a catheter axis, wherein the catheter directs a radiation of first wavelength and a radiation of second wavelength from its distal end thereof towards a sample as a light beam transverse to the catheter axis, and collects at its distal end thereof, from a plurality of locations of the sample, backscattered radiation of first wavelength in response to irradiation with the radiation of first wavelength and a radiation of third wavelength emitted in response to irradiation with the radiation of second wavelength;
detecting, with a first detector operatively coupled to the catheter, an intensity of the radiation of third wavelength and, with a second detector operatively coupled to the catheter, an intensity of the backscattered radiation of first wavelength collected by the catheter from each of the plurality of locations of the sample;

acquiring data about the intensity of the radiation of third wavelength and data about the intensity of the backscattered radiation of first wavelength;

based on the data about the intensity of the backscattered radiation of first wavelength, calculating, using a processor operatively coupled to the first detector and the second detector, an angle $\alpha$ at which the radiation of second wavelength is incident on each of the plurality of locations of the sample; and adjusting, using the processor, the intensity of the radiation of third wavelength detected by the first detector using a calibration factor $g(\alpha)$, wherein the calibration factor $g(\alpha)$ is a function of the angle $\alpha$ calculated for each of the plurality of locations, wherein the processor adjusts the intensity of the radiation of third wavelength by multiplying the detected intensity of the radiation of third wavelength by the calibration factor $g(\alpha)$ obtained from the backscattered radiation of first wavelength at each of the plurality of locations, wherein the processor calculates the angle $\alpha$ by combining values of an axial rotation angle $\alpha_a$ measured along an axial plane of the sample, and a transversal angle $\alpha_t$ measured along a transversal plane of the sample, wherein the axial plane is perpendicular to the catheter axis and the transversal plane is parallel to the catheter axis, and wherein the transversal angle $\alpha_t$ is measured along the transversal plane of the sample between a line normal to the sample surface and the light beam transverse to the catheter axis along which the radiation is directed from the catheter to the sample, and the axial rotation angle $\alpha_a$ is measured along the axial plane of the sample between a line normal to the sample surface and the light beam transverse to the catheter axis along which the radiation is directed from the catheter to sample.

13. A non-transitory computer-readable storage medium storing thereon computer executable code, which when executed by a processor, causes a computer to perform the method according to claim 12.

* * * * *